United States Patent
Spurlock

(10) Patent No.: US 6,297,027 B1
(45) Date of Patent: Oct. 2, 2001

(54) BOVINE LEPTIN PROTEIN, NUCLEIC ACID SEQUENCES CODING THEREFOR AND USES THEREOF

(75) Inventor: Michael E. Spurlock, Pacific, MO (US)

(73) Assignee: Purina Mills, Inc., St. Louis, MO (US)

( * ) Notice: Subject to any disclaimer, the term of this patent is extended or adjusted under 35 U.S.C. 154(b) by 0 days.

(21) Appl. No.: 08/688,908

(22) Filed: Jul. 31, 1996

(51) Int. Cl.[7] .......................... C07K 14/435; C12N 1/21; C12N 15/12; C12N 15/63

(52) U.S. Cl. .................. 435/69.1; 435/252.3; 435/320.1; 435/325; 530/350; 536/235

(58) Field of Search ................................. 536/23.5, 24.5; 435/320.1, 240.2, 252.3, 325, 69.1; 530/350

(56) References Cited

U.S. PATENT DOCUMENTS

| | | |
|---|---|---|
| 3,507,662 | 4/1970 | Leroy et al. . |
| 3,619,200 | 11/1971 | Ferguson et al. . |
| 3,695,891 | 10/1972 | Fox . |
| 4,237,224 | 12/1980 | Cohen et al. . |
| 4,358,535 | 11/1982 | Falkow et al. . |
| 4,376,110 | 3/1983 | David et al. . |
| 4,377,576 | 3/1983 | Schmidt et al. . |
| 4,446,237 | 5/1984 | Berninger . |
| 4,563,417 | 1/1986 | Albarella et al. . |
| 4,581,333 | 4/1986 | Kourilsky et al. . |
| 4,582,788 | 4/1986 | Erlich . |
| 4,582,789 | 4/1986 | Sheldon, III et al. . |
| 4,683,194 | 7/1987 | Saiki et al. . |
| 4,683,202 | 7/1987 | Mullis . |
| 5,089,397 | 2/1992 | Kushner et al. . |
| 5,268,295 | 12/1993 | Serrero . |
| 5,362,629 | 11/1994 | Shreiber et al. . |
| 5,585,479 | * 12/1996 | Hoke et al. . |
| 5,935,810 | 8/1999 | Friedman et al. ................. 435/69.1 |
| 6,001,968 | 12/1999 | Friedman et al. ................. 530/350 |

FOREIGN PATENT DOCUMENTS

| | | |
|---|---|---|
| 050424 | 4/1982 | (EP) . |
| 084796 | 8/1983 | (EP) . |
| 119448 | 9/1984 | (EP) . |
| 144914 | 6/1985 | (EP) . |
| 201184 | 12/1986 | (EP) . |
| 237362 | 9/1987 | (EP) . |
| 258017 | 3/1988 | (EP) . |
| WO 93/03050 | 2/1993 | (WO) . |
| WO 93/16183 | 8/1993 | (WO) . |

OTHER PUBLICATIONS

Leroy, Pascale, et al., "Expression of Ob Gene in Adipose Cells", *The Journal of Biological Chemistry*, vol. 271, No. 5, Issue of Feb. 2, pp. 2365–2368, 1996.

Saladin, Regis, et al., "Transient Increase in Obese Gene Expression After Food Intake or Insulin Administration", *Nature*, vol. 377, pp. 527–529, Oct. 12, 1995.

Campfield, L. Arthur, et al., "Recombinant Mouse Ob Protein: Evidence For a Peripheral Signal Linking Adiposity and Central Neural Networks", *Science*, vol. 269, pp. 546–549, Jul. 28, 1995.

Halaas, Jeffery L., et al., "Weight–reducing Affects of the Plasma Protein Encoded by the Obese Gene", *Science*, vol. 269, pp. 543–546, Jul. 28, 1995.

Pelleymounter, Mary Ann, et al., "Effects of the Obese Gene Product on Body Weight Regulation in Ob/Ob Mice", *Science*, vol. 269, pp. 540–543, Jul. 28, 1995.

Maffei, Margherita, et al., "Increased Expression in Adipocytes of Ob RNA in Mice with Lesions of the Hypothalamus and with Mutations at the DB Locus", *Proc. Natl. Acad. Sci. USA*, vol. 92, pp. 6957–6960, Jul. 1995.

Zhang, Yiying, et al., "Positional Cloning of the Mouse Obese Gene and its Human Homologue", *Nature*, vol. 372, pp. 425–432, Dec. 1, 1994.

Better, Marc, et al., "*Escherichia Coli* Secretion of an Active Chimeric Antibody Fragment", *Science*, vol. 240, May 20, 1988.

Liu, Alvin Y. et al., "Chimeric Mouse–human IGG1 Antibody that can Mediate Lysis of Cancer Cells", *Proc. Natl. Acad. Sci. USA*, vol. 84, pp. 3439–3443, May 1987.

Chomczynski, Piotr, & Sacchi, Nicoletta, "Single–step Method of RNA Isolation by Acid Guanidinium Thiocyanate–Phenol–Chloroform Extraction", *Analytical Biochemistry*, 162, 156–159 (1987).

Boulianne, Gabrielle L., et al., "Production of Functional Chimaeric Mouse/Human Antibody", *Nature*, vol. 312, Dec. 13, 1984.

(List continued on next page.)

Primary Examiner—Christine J. Saoud
(74) Attorney, Agent, or Firm—Whyte Hirschboeck Dudek SC

(57) ABSTRACT

A bovine adipocyte-specific polypeptide, termed leptin, is expressed in the fat tissue of cattle. Expression may be altered in over fat cattle, or expression may be in the form of a protein of lesser biological activity relative to that of leaner cattle. The bovine adipocyte polypeptide, DNA and RNA molecules coding therefor, methods for its preparation, and antibodies specific for the polypeptide are disclosed. Methods for determining the susceptibility of cattle to fat deposition are based on measuring the levels of the bovine adipocyte polypeptide in a biological fluid or tissue extract or by measuring mRNA encoding the bovine adipocyte polypeptide in cells of the subject. Methods of evaluating an agent related to the deposition of fat in cattle comprise contacting the agent with an adipocyte in vitro and measuring the amount of the bovine adipocyte polypeptide or mRNA that is produced by the adipocyte. Methods of limiting fat deposition include administering leptin or leptin DNA, and methods of altering intake include administering leptin, leptin DNA, or an antibody directed against leptin.

14 Claims, 10 Drawing Sheets

OTHER PUBLICATIONS

Morrison, Sherie L., et al., "Chimeric Human Antibody Molecules: Mouse Antigen–binding Domains with Human Constant Region Domains", *Proc. Natl. Acad. Sci. USA*, vol. 81, pp. 6851–6855, Nov. 1984.

Cabilly, Shmuel, et al., "Genration of Antibody Activity From Immunoglobulin Polypeptide Chains Produced in *Escherichia Coli*", *Proc. Natl. Acad. Sci. USA*, vol. 81, pp. 3273–3277, Jun. 1984.

Wahl, Richard L., "Improved Radioimaging and Tumor Localization with Monoclonal F(ab')2", *J. Nucl. Med.* 24:316–325, 1983.

De St. Groth, S. Fazekas, & Scheidegger, Doris, "Production of Monoclonal Antibodies: Strategy and Tactics", *Journal of Immunological Methods*, 35 (1980) 1–21.

Kohler, G. & Milstein, C., "Continuous Cultures of Fused Cells Secreting Antibody of Predefined Specificity", *Nature*, vol. 256, pp. 495–497 Aug. 7, 1975.

Zhang Y, et al. "Positional cloning of the mouse obese gene and its homologue." Nature 372:: 425–432, 1994.*

* cited by examiner

FIGURE 1

```
         10         20         30         40         50         60
AGGCCGTGCC TATCCAGAAA GTCCAGGATG ACACCAAAAC CCTCATCAAG ACAATTGTCA
    V  P    I  Q  K   V  Q  D    D  T  K  T   L  I  K    T  I  V
         70         80         90        100        110        120
CCAGGATCAA TGACATCTCA CACACGCAGT CCGTCTCCTC CAAACAGAGG GTCACTGGTT
 T  R  I  N  D  I  S   H  T  Q    S  V  S  S   K  Q  R   V  T  G
        130        140        150        160        170        180
TGGACTTCAT CCCTGGGCTC CACCCTCTCC TGAGTTTGTC CAAGATGGAC CAGACATTGG
 L  D  F  I  P  G  L    H  P  L   L  S  L  S   K  M  D   Q  T  L
        190        200        210        220        230        240
CGATCTACCA ACAGATCCTC ACCAGTCTGC CTTCCAGAAA TGTGGTCCAA ATATCCAATG
 A  I  Y  Q   Q  I  L   T  S  L    P  S  R  N   V  V  Q   I  S  N
        250        260        270        280        290        300
ACCTGGAGAA CCTCCGGGAC CTTCTCCACC TGCTGGCCGC CTCCAAGAGC TGCCCCTTGC
 D  L  E  N   L  R  D   L  L  H    L  L  A  A   S  K  S   C  P  L
        310        320        330        340        350        360
CGCAGGTCAG GGCCCTGGAG AGCTTGGAGA GCTTGGGTGT CGTCCTGGAA GCCTCCCTCT
 P  Q  V  R   A  L  E   S  L  E    S  L  G  V   V  L  E   A  S  L
        370        380        390        400        410        420
ACTCCACCGA GGTGGTGGCC CTGAGCCGGC TGCAGGGGTC ACTACAGGAC ATGTTGCGGC
 Y  S  T  E   V  V  A   L  S  R    L  Q  G  S   L  Q  D   M  L  R
        430        440        450
AGCTGGACCT CAGCCCTGAA TGCAGCGCT.
 Q  L  D  L   S  P  E   C
```

FIGURE 2A

```
Query:    1 AGGCCGTGCCTATCCAGAAAGTCCAGGATGACACCAAAACCCTCATCAAGACAATTGTCA  60
            | || |||||| ||||| ||||||||| |||||||||||||||||||||||||||||||
Sbjct:   59 AAGCTGTGCCCATCCAAAAAGTCCAAGATGACACCAAAACCCTCATCAAGACAATTGTCA 118

Query:   61 CCAGGATCAATGACATCTCACACACGCAGTCCGTCTCCTCCAAACAGAGGGTCACTGGTT 120
            ||||||||||||||||| ||||||||||||| ||||||||||||||||| ||||| ||||
Sbjct:  119 CCAGGATCAATGACATTTCACACACGCAGTCAGTCTCCTCCAAACAGAAAGTCACCGGTT 178

Query:  121 TGGACTTCATCCCTGGGCTCCACCCTCTCCTGAGTTTGTCCAAGATGGACCAGACATTGG 180
            ||||||||| || ||||||||||||| |||||  || ||||||||||||||||||| ||
Sbjct:  179 TGGACTTCATTCCTGGGCTCCACCCCATCCTGACCTTATCCAAGATGGACCAGACACTGG 238

Query:  181 CGATCTACCAACAGATCCTCACCAGTCTGCCTTCCAGAAATGTGGTCCAAATATCCAATG 240
            |  |||||||||||||||||||||| |||||||||||||| ||| |||||||||||| |
Sbjct:  239 CAGTCTACCAACAGATCCTCACCAGTATGCCTTCCAGAAACGTGATCCAAATATCCAACG 298

Query:  241 ACCTGGAGAACCTCCGGGACCTTCTCCACCTGCTGGCCGCCTCCAAGAGCTGCCCCTTGC 300
            ||||||||||||||||||| |||| ||| |||||||| ||||| |||||||||| ||||
Sbjct:  299 ACCTGGAGAACCTCCGGGATCTTCTTCACGTGCTGGCCTTCTCTAAGAGCTGCCACTTGC 358

Query:  301 CGCAGGTCAGGGCCCTGGAGAGCTTGGAGAGCTTGGGTGTCGTCCTGGAAGCCTCCCTCT 360
             | || |||  ||||||| |||||| ||| |||| |  ||||||||||| ||   ||
Sbjct:  359 CCTGGGCCAGTGGCCTGGAGACCTTGGACAGCCTGGGGGTGTCCTGGAAGCTTCAGGCT 418

Query:  361 ACTCCACCGAGGTGGTGGCCCTGAGCCGGCTGCAGGGGTCACTACAGGACATGTTGCGGC 420
            ||||| | ||||||||||||||||| ||||||||||||||| || |||||||| | |||
Sbjct:  419 ACTCCACAGAGGTGGTGGCCCTGAGCAGGCTGCAGGGGTCTCTGCAGGACATGCTGTGGC 478

Query:  421 AGCTGGACCTCAGCCCTGAATGCAG 445
            |||||||||||||||||||  ||| |
Sbjct:  479 AGCTGGACCTCAGCCCTGGGTGCTG 503
```

Query = bovine leptin cDNA
Sbjct = human leptin cDNA

FIGURE 2B

```
Query:       1 AGGCCGTGCCTATCCAGAAAGTCCAGGATGACACCAAAACCCTCATCAAGACAATTGTCA   60
               | ||  ||||||||||||||||||||||||||||||||||||||||||||||||| ||||||
Sbjct:      59 AAGCAGTGCCTATCCAGAAAGTCCAGGATGACACCAAAACCCTCATCAAGACCATTGTCA  118

Query:      61 CCAGGATCAATGACATCTCACACACG   86
               |||||||||||||||||| |||||||||
Sbjct:     119 CCAGGATCAATGACATTTCACACACG  144

Query:      87 CAGTCCGTCTCCTCCAAACAGAGGGTCACTGGTTTGGACTTCATCCCTGGGCTCCACCCT  146
               ||||| ||  |||  ||||  ||||||||||||| |||||||||| |||||||| |||||
Sbjct:    1876 CAGTCGGTATCCGCCAAGCAGAGGGTCACTGGCTTGGACTTCATTCCTGGGCTTCACCCC 1935

Query:     147 CTCCTGAGTTTGTCCAAGATGGACCAGACATTGGCGATCTACCAACAGATCCTCACCAGT  206
                | |||||||||||||||||||||||||| |||||||| |||| |||||| ||||||||||
Sbjct:    1936 ATTCTGAGTTTGTCCAAGATGGACCAGACTCTGGCAGTCTATCAACAGGTCCTCACCAGC 1995

Query:     207 CTGCCTTCCAGAAATGTGGTCCAAATATCCAATGACCTGGAGAACCTCCGGGACCTTCTC  266
               ||||||||| |||||||| || || ||||||||||||||||||| ||||| |||| |||
Sbjct:    1996 CTGCCTTCCCAAAATGTGCTGCAGATAGCCAATGACCTGGAGAATCTCCGAGACCTCCTC  2055

Query:     267 CACCTGCTGGCCGCCTCCAAGAGCTGCCCCTTGCCGCAGGTCAGGGCCCTGGAGAGCTTG  326
               || ||||||||||| ||||||||||||| ||||| |||||||||| || ||||| ||
Sbjct:    2056 CATCTGCTGGCCTTCTCCAAGAGCTGCTCCCTGCCTCAGACCAGTGGCCTGCAGAAGCCA  2115

Query:     327 GAGAGCTTGGGTGTCGTCCTGGAAGCCTCCCTCTACTCCACCGAGGTGGTGGCCCTGAGC  386
               |||||| ||| || |||||||||||||||| ||||||||| |||||||||||| |||||
Sbjct:    2116 GAGAGCCTGGATGGCGTCCTGGAAGCCTCACTCTACTCCACAGAGGTGGTGGCTTTGAGC  2175

Query:     387 CGGCTGCAGGGGTCACTACAGGACATGTTGCGGCAGCTGGACCTCAGCCCTGAATGCAG   445
               ||||||||||| || || ||||||| || || || |||| | |||||||||||||| |
Sbjct:    2176 AGGCTGCAGGGCTCTCTGCAGGACATTCTTCAACAGTTGGATGTTAGCCCTGAATGCTG  2234
```

Query = bovine leptin cDNA
Sbjct = murine leptin cDNA

FIGURE 3A

```
                        10        20        30      —39
C1con1          VPIQKVQDDTKTLIKTIVTRINDISHTQSVSSKQRVTGL
                |||||||||||||||||||||||||||||||||:||||
Ob_Hum  MHWGTLCGFLWLWPYLFYVQAVPIQKVQDDTKTLIKTIVTRINDISHTQSVSSKQKVTGL
            10        20        30        40        50        60

40        50        60        70        80        90      99
C1con1  DFIPGLHPLLSLSKMDQTLAIYQQILTSLPSRNVVQISNDLENLRDLLHLLAASKSCPLP
        ||||||||:|:||||||||:|||||||:|||||:||||||||||||||||:|| ||||:||
Ob_Hum  DFIPGLHPILTLSKMDQTLAVYQQILTSMPSRNVIQISNDLENLRDLLHVLAFSKSCHLP
            70        80        90       100       110       120

100       110       120       130       140
C1con1  QVRALESLESLGVVLEASLYSTEVVALSRLQGSLQDMLRQLDLSPEC
        :::|||:|:|||  |||||  ||||||||||||||||||:|||||||:|
Ob_Hum  WASGLETLDSLGGVLEASGYSTEVVALSRLQGSLQDMLWQLDLSPGC
           130       140       150       160
```

C1con1 = predicted bovine leptin amino acid sequence
Ob Hum = human leptin amino acid sequence

FIGURE 3B

```
                          10        20        30      39
Clcon1           VPIQKVQDDTKTLIKTIVTRINDISHTQSVSSKQRVTGL
                 ||||||||||||||||||||||||||||||:|||||||
Ob_Mou  MCWRPLCRFLWLWSYLSYVQAVPIQKVQDDTKTLIKTIVTRINDISHTQSVSAKQRVTGL
            10        20        30        40        50        60

40        50        60        70        80        90      99
Clcon1  DFIPGLHPLLSLSKMDQTLAIYQQILTSLPSRNVVQISNDLENLRDLLHLLAASKSCPLP
        ||||||||:||||||||||||:|||:||||||||:||:||:|||||||||||| ||||:||
Ob_Mou  DFIPGLHPILSLSKMDQTLAVYQQVLTSLPSQNVLQIANDLENLRDLLHLLAFSKSCSLP
            70        80        90       100       110       120

100       110       120       130       140
Clcon1  QVRALESLESLGVVLEASLYSTEVVALSRLQGSLQDMLRQLDLSPEC
        |:::|::  |||:  ||||||||||||||||||||||:|:|||:||||
Ob_Mou  QTSGLQKPESLDGVLEASLYSTEVVALSRLQGSLQDILQQLDVSPEC
           130       140       150       160
```

Clcon1 = predicted bovine leptin amino acid sequence
Ob_Mou = murine leptin amino acid sequence

FIGURE 4

1 VPIQKVQDDTKTLIKTIVTRINDISHTQSV 30

FIGURE 5A

Query:   1   VPIQKVQDDTKTLIKTIVTRINDISHTQSV 30

Sbjct:  22   VPIQKVQDDTKTLIKTIVTRINDISHTQSV 51

Query = actual bovine leptin amino acid sequence
Sbjct = human leptin amino acid sequence

FIGURE 5B

```
Query:    1  VPIQKVQDDTKTLIKTIVTRINDISHTQSV  30

Sbjct:   22  VPIQKVQDDTKTLIKTIVTRINDISHTQSV  51
```

```
Query = actual bovine leptin amino acid sequence
Sbjct = murine leptin amino acid sequence
```

BOVINE LEPTIN PROTEIN, NUCLEIC ACID SEQUENCES CODING THEREFOR AND USES THEREOF

BACKGROUND OF THE INVENTION

1. Field of the Invention

This invention relates to the regulation of energy intake and metabolism in growing, finishing, lactating or nonlactating, and gestating bovine. More specifically, it relates to a specific bovine polypeptide termed leptin which is secreted by adipocytes or other cell types and which influences energy intake and metabolism, fat deposition, and weight gain in bovine. In addition, this invention relates to the nucleotide sequences encoding the bovine leptin polypeptide, the antibodies directed against the bovine leptin polypeptide, and methods to determine susceptibility to fat deposition, alter energy intake, and minimize excessive fat deposition in bovine.

2. Description of the Background Art

Obesity has been declared a public health hazard by the National Institutes of Health and has prompted the food animal industry to seek methods of limiting fat deposition in food animals. Additionally, the energetic cost of having food animals convert feed energy to fat rather than lean tissue provides considerable incentive to develop technology to facilitate the efficient production of leaner meat products and to accurately match the nutrient content of the diet to the nutrient needs of the animal. To combat these health and production problems, both prophylactic and therapeutic approaches are necessary. For prophylactic purposes, it would be useful to be able to predict and measure the propensity or susceptibility to excessive fat deposition. For therapeutic purposes, it would be of great benefit to improve current methods of minimizing the deposition of feed energy as fat in the adipocyte. Currently, neither of these desired objectives has been achieved completely.

Proteins from genes expressed only (or predominantly) in adipose tissue and for which the level of expression can be related to fat deposition serve as prime targets for approaches directed toward prediction of fat accretion potential and the control of fat deposition. For example, a mammalian adipocyte-specific polypeptide, termed p154, was reported in U.S. Pat. No. 5,268,295 to Serrero, which is incorporated in its entirety herein by reference, as being expressed in high quantities in adipogenic cell lines after cell differentiation and is abundant in the fat pads of normal and genetically obese mice. To date, however, there are no known reports of adipocyte-specific proteins expressed at different levels in fat cattle as compared with normal controls.

Leptin, the protein produced by the leptin (ob) gene, is possibly related to fat deposition in bovine because research has shown that mutations in genetically (ob/ob) obese mice resulting in excessive fat deposition are associated with altered expression of the leptin gene. Furthermore, at least one restriction fragment length polymorphism (RFLP) has been identified and related to the fat phenotype (Zhang et al., 1994, Nature 371:425). The leptin gene is expressed specifically in the terminally differentiated adipocyte (Maffei et al., 1995, Proc. Natl. Acad. Sci. 92:6957; Leroy et al., 1996, J. Biol. Chem. 271(5):2365). Additionally, leptin is a regulator of feed intake (Pellymounter et al.,1995, Sci. 269:540; Halaas et al., 1995, Sci. 269:543; Campfield et al., 1995, Sci. 269:546).

Although the murine leptin gene has been positionally cloned and a cDNA sequence reported (Nature 371:425), the bovine leptin cDNA or genomic sequence was not available prior to initiation of this project. Thus, the insights obtained with respect to bovine metabolism were not accessible to bovine systems. Furthermore, the biologically active purified bovine protein (i.e., leptin) has not been obtained.

SUMMARY OF THE INVENTION

The present invention provides gene sequences, peptides, antibodies, and methods of using them which permit the prediction and modulation of fat deposition and regulation of feed intake (i.e. appetite), in the bovine species.

In one aspect, this invention is directed to a bovine adipocyte polypeptide, the bovine leptin protein, substantially free of other bovine proteins, or a functional derivative thereof. The present invention includes a bovine adipocyte polypeptide consisting essentially of at least about 8 amino acids of the amino acid sequence depicted in FIGS. 1 and 3–5 (SEQ ID NOS:4, 7 and 8), or a functional derivative thereof.

The present invention is also directed to a single or double stranded DNA molecule or an RNA molecule consisting essentially of a nucleotide sequence that encodes the above polypeptide or a functional derivative thereof, the DNA or RNA molecule being substantially free of other bovine DNA or RNA sequences. The DNA molecule is preferably a single or double stranded DNA molecule having a nucleotide sequence consisting essentially of at least about 20 nucleotides of the nucleotide sequence depicted in FIGS. 1 and 2 (SEQ ID NOS:3) or a sequence complementary to at least part of the nucleotide sequence depicted in FIGS. 1 and 2 (SEQ ID NOS:4), or a functional equivalent thereof, substantially free of other bovine DNA sequences. The RNA molecule is preferably an mRNA sequence encoding the above bovine adipocyte polypeptide, or a functional derivative thereof.

Included in the invention is a DNA molecule as described above which is cDNA or genomic DNA, preferably in the form of an expressible vehicle or plasmid.

The present invention is also directed to hosts transformed or transfected with the above DNA molecules, including a prokaryotic host, preferably a bacterium, a eukaryotic host such as a yeast cell, or a mammalian cell.

The present invention also provides a process for preparing a bovine adipocyte polypeptide or functional derivative as described above, the process comprising the steps of: (a) culturing a host capable of expressing the polypeptide under culture conditions; (b) expressing the polypeptide; and (c) recovering the polypeptide from the culture.

Also included in the present invention is a method for detecting the presence of a nucleic acid molecule having the sequence of the DNA molecule described above, or a complementary sequence, in a nucleic acid-containing sample, the method comprising: (a) contacting the sample with an oligonucleotide probe complementary to the sequence of interest under hybridizing conditions; and (b) measuring the hybridization of the probe to the nucleic acid molecule, thereby detecting the presence of the nucleic acid molecule. The above method may additionally comprise before step (a): (c) selectively amplifying the number of copies of the nucleic acid sequence.

Another embodiment of this invention is an antibody specific for an epitope of the bovine adipocyte polypeptide, or functional derivative, either polyclonal or monoclonal. Also intended is a method for detecting the presence or measuring the quantity of the bovine adipocyte polypeptide leptin in a biological sample, comprising contacting the sample with the above antibody and detecting the binding of the antibody to an antigen in the sample, or measuring the quantity of antibody bound.

The present invention includes methods for determining the susceptibility of cattle to fat deposition which comprises removing a biological sample from a subject and measuring therein the amount of the polypeptide or mRNA coding therefor, where the amount of the polypeptide or mRNA is related to susceptibility. The present invention also includes methods for determining the susceptibility of a subject to fat deposition which comprises removing a biological sample, extracting the DNA, digesting the DNA with restriction endonucleases, probing the sample with an oligonucleotide probe, separating the resulting fragments by gel electrophoresis, and relating the number of bands (banding pattern) generated by restriction enzyme digestion to fat deposition (i.e., RFLP techniques).

Another method provided herein is for evaluating the efficacy of a drug (or other agent) directed to the regulation of fat deposition and feed intake which comprises contacting the drug being tested with an adipocyte culture in vitro and measuring the amount of the adipocyte polypeptide or mRNA that is produced, the efficacy of the drug being related to changing the production of the polypeptide or mRNA.

BRIEF DESCRIPTION OF THE DRAWINGS

FIG. 1 depicts the bovine leptin cDNA nucleotide sequence (top) (SEQ ID NO:3) and predicted amino acid sequence (bottom) for the coding region minus the secretory signal.

FIG. 2A shows a comparison of the bovine leptin cDNA nucleotide sequence (SEQ ID NO:3) with the human nucleotide sequence.

FIG. 2B shows a comparison of the bovine leptin cDNA nucleotide sequence with the murine nucleotide sequence (SEQ ID NO:3).

FIG. 3A shows a comparison of the predicted bovine leptin amino acid sequence (SEQ ID NO:4) with the human leptin amino acid sequence.

FIG. 3B shows a comparison of the predicted bovine leptin amino acid sequence (SEQ ID NO:4) with the murine leptin amino acid sequence.

FIG. 4 depicts a portion of the actual bovine leptin amino acid sequence (SEQ ID NO:5) which is an N-terminal sequence comprising 30 amino acids.

FIG. 5A shows a comparison of the actual bovine leptin amino acid sequence (SEQ ID NO:7) with the human leptin amino acid sequence.

FIG. 5B shows a comparison of the actual bovine leptin amino acid sequence (SEQ ID NO:8) with the murine leptin amino acid sequence.

DETAILED DESCRIPTION OF PREFERRED EMBODIMENTS

Figure 6:
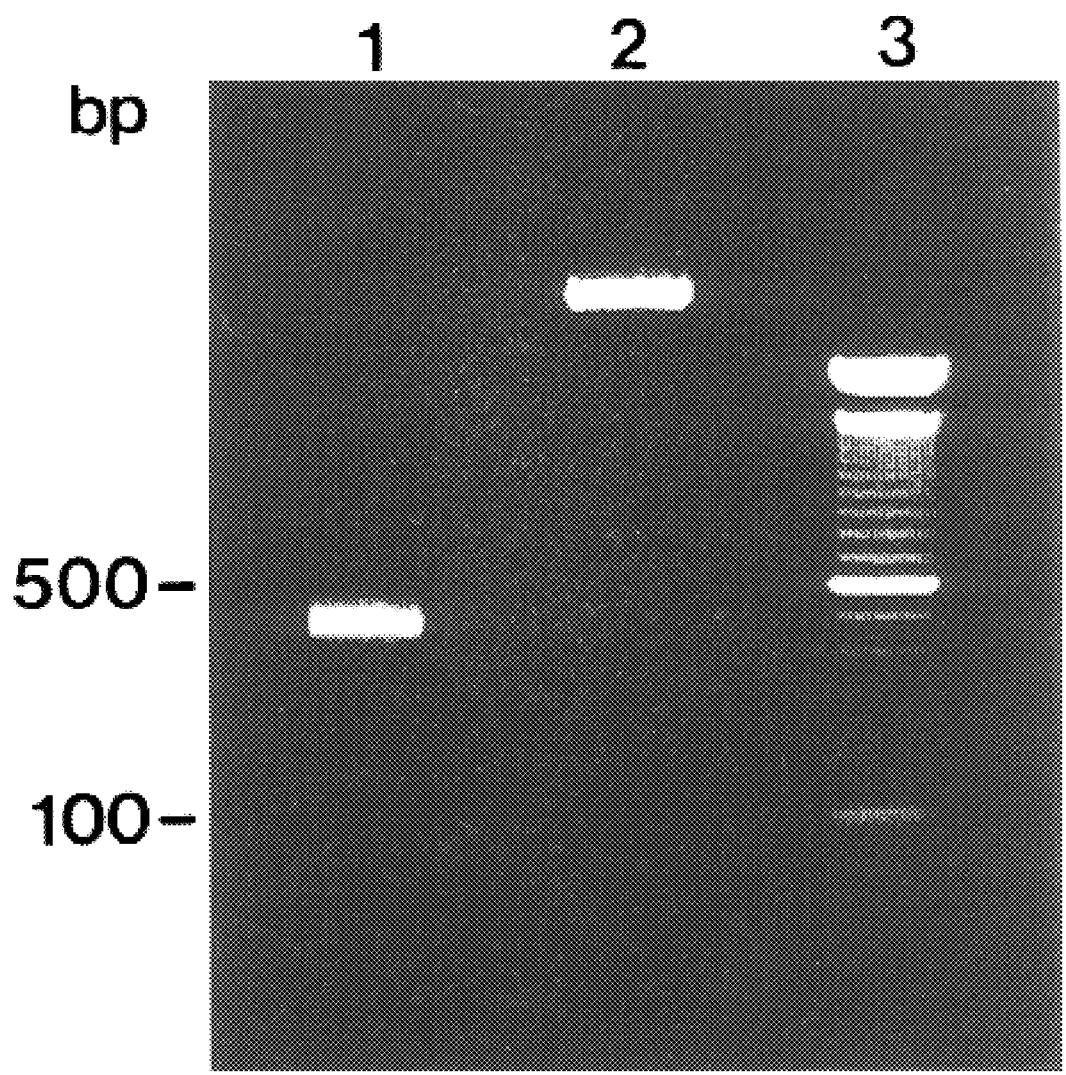
FIG. 6 shows that a band of 449 base pairs was obtained from a PCR-amplified bovine single-stranded cDNA.

The present invention is directed to DNA and RNA molecules that encode a bovine adipocyte polypeptide termed "leptin", or a functional derivative thereof, and the bovine leptin protein itself, or a functional derivative thereof. The bovine leptin protein is useful for the regulation of feed intake, energy metabolism, and fat deposition in cattle. Such objectives can be achieved by administering recombinant or purified leptin, altering the expression of the bovine leptin gene or administering an antibody directed against the bovine leptin protein to achieve neutralization, depending upon the desired result. The bovine leptin DNA, RNA, and protein, or functional derivatives thereof, and antibodies specific for the protein are used in assays to predict the potential for fat deposition in cattle. These molecules can also be utilized in the development of commercially valuable technology for altering feed intake and regulating fat deposition in cattle, and for matching the nutrient content of the diet to the nutrient needs of the cattle.

In its first aspect, the present invention provides a bovine adipocyte polypeptide termed "leptin". The term "polypeptide" as used herein is intended to include not only the bovine leptin protein, and functional derivatives thereof, but also amino acid sequences having additional components, e.g., amino acid sequences having additional components such as a sugar, as in a glycopeptide, or other modified protein structures known in the art.

The polypeptide of this invention has an amino acid sequence as depicted in FIGS. 1 and 3–5 (SEQ ID NOS:4, 7 and 8). Also intended within the scope of the present invention is any peptide having at least about 8 amino acids present in the above-mentioned sequence. Sequences of this length are useful as antigens and for making immunogenic conjugates with carriers for the production of antibodies specific for various epitopes of the entire protein. Such peptides are also useful in screening such antibodies and in the methods of the present invention directed to detection of the leptin protein in biological samples. It is well-known in the art that peptides of about 8 amino acids are useful in generation of antibodies to larger proteins of biological interest.

The polypeptide of this invention is sufficiently large to comprise an antigenically distinct determinant, or epitope, which can be used as an immunogen to produce antibodies against leptin, or a functional derivative thereof, and to test such antibodies. The polypeptide of this invention may also exist covalently or noncovalently bound to another molecule. For example, it may be fused (i.e., a fusion protein) to one or more other polypeptides via one or more peptide bonds.

One embodiment includes the polypeptide substantially free of other bovine peptides. The polypeptide of the present invention may be biochemically or immunochemically purified from cells, tissues, or a biological fluid. Alternatively, the polypeptide can be produced by recombinant means in a prokaryotic or eukaryotic host cell.

"Substantially free of other bovine polypeptides" reflects the fact that because the gene for the bovine adipocyte polypeptide of interest can be cloned, the polypeptide can be expressed in a prokaryotic or eukaryotic organism, if desired. Methods are also well known for the synthesis of polypeptides of a desired sequence on solid phase supports and their subsequent separation from the support. Alternatively, the protein can be purified from tissue or fluids of the bovine in which it naturally occurs so that it is purified away from at least 90 percent (on a weight basis), and from even at least 99 percent if desired, of other bovine polypeptides and is therefore substantially free of them. That can be achieved by subjecting the tissue or fluids to standard protein purification techniques such as immunoadsorbent columns bearing monoclonal antibodies reactive against the protein. Alternatively, the purification from such tissue or fluids can be achieved by a combination of standard methods, such as ammonium sulfate precipitation, molecular sieve chromatography, and ion exchange chromatography.

As alternatives to a native purified or recombinant bovine adipocyte polypeptide molecule, functional derivatives of the bovine adipocyte polypeptide may be used. As used herein, the term "functional derivative" refers to any "fragment", "variant", "analog", or "chemical derivative" of the bovine adipocyte polypeptide that retains at least a portion of the function of the bovine adipocyte polypeptide which permits its utility in accordance with the present invention.

A "fragment" of the bovine adipocyte polypeptide as used herein refers to any subset of the molecule, that is, a shorter peptide.

A "variant" of the bovine adipocyte polypeptide as used herein refers to a molecule substantially similar to either the entire peptide or a fragment thereof. Variant peptides may be conveniently prepared by direct chemical synthesis of the variant peptide, using methods well-known in the art. Alternatively, amino acid sequence variants of the peptide can be prepared by mutations in the DNA which encodes the synthesized peptide (again using methods well-known in the art). Such variants include, for example, deletions from, or insertions or substitutions of, residues within the amino acid sequence. Any combination of deletion, insertion, and substitution may also be made to arrive at the final construct, provided that the final construct possesses the desired activity. Obviously, the mutations that will be made in the DNA encoding the variant peptide must not alter the reading frame and preferably will not create complementary regions that could produce secondary mRNA structures.

An "analog" of the bovine adipocyte polypeptide as used herein refers to a non-natural molecule substantially similar to either the entire molecule or a fragment thereof.

A "chemical derivative" of the bovine adipocyte polypeptide or peptide as used herein contains additional chemical moieties not normally a part of the polypeptide. Covalent modifications are included within the scope of this invention. Such modifications may be introduced into the molecule by reacting targeted amino acid residues with an organic derivatizing agent that is capable of reacting with selected side chains or terminal residues.

The polypeptide of the present invention is encoded by a nucleic acid molecule, one strand of which has the nucleotide sequence shown in FIGS. 1 and 2 (SEQ ID NO:3). The present invention is directed to a DNA sequence encoding the polypeptide, or a functional derivative thereof, substantially free of other bovine DNA sequences. Such DNA may be single-stranded (i.e., sense, antisense or cDNA sequence) or double-stranded. The DNA sequence should preferably have about 20 or more nucleotides to allow hybridization to another polynucleotide. In order to achieve higher specificity of hybridization, characterized by the absence of hybridization to sequences other than those encoding the polypeptide, or a functional derivative thereof, a length of at least about 50 nucleotides is preferred.

The present invention is also directed to an RNA molecule comprising a mRNA sequence encoding the polypeptide of this invention, or a functional derivative thereof.

The present invention is further directed to the above DNA molecules which are functional in recombinant expression systems utilizing as hosts transfected or transformed with the vehicles and capable of expressing the polypeptide. Such hosts may be prokaryotic or eukaryotic. The DNA can be incorporated in to the host organism by transformation, transduction, transfection, or a related process known in the art.

In addition to a DNA and mRNA sequence encoding the bovine adipocyte polypeptide molecule, this invention provides methods for the expression of the nucleic acid sequences. Further, the genetic sequences and oligonucleotides of the invention allow the identification and cloning of additional, yet undiscovered adipocyte polypeptides having sequence homology to the bovine adipocyte polypeptide described herein.

The recombinant DNA molecules of the present invention can be produced through any of a variety of means, such as, for example, DNA or RNA synthesis, or more preferably, by application of recombinant DNA techniques. Techniques for synthesizing such molecules are disclosed by, for example, Wu, R., et al., Prog. Nucl. Acid. Res. Molec. Biol. 21:101–141(1978), which is incorporated herein by reference. Procedures for constructing recombinant molecules in accordance with the above-described method are disclosed by Sambrook et al. Molecular Cloning: A Laboratory Manual, Second Edition, Cold Spring Harbor Press, Cold Spring Harbor, N.Y. (1989), which is herein incorporated by reference.

Oligonucleotides representing a portion of the bovine adipocyte polypeptide of this invention are useful for screening for the presence of genes encoding such proteins and for the cloning of bovine adipocyte polypeptide genes. Techniques for synthesizing such oligonucleotides are disclosed by, for example, Wu, R., et al.. Prog. Nucl. Acid. Res. Molec. Biol. 21:101–141 (1978).

A suitable oligonucleotide, or set of oligonucleotides, which is capable of encoding a fragment of the bovine adipocyte polypeptide gene of this invention (or which is complementary to such an oligonucleotide, or set of oligonucleotides) is identified, synthesized, and hybridized by means well known in the art, against a DNA or, more preferably, a cDNA preparation derived from cells which are capable of expressing the bovine adipocyte polypeptide gene. Single stranded oligonucleotide molecules complementary to the "most probable" bovine adipocyte polypeptide-encoding sequences can be synthesized using procedures which are well known to those of ordinary skill in the art (See e.g., U.S. Pat. No. 5,268,295). Additionally, DNA synthesis may be achieved through the use of automated synthesizers. Techniques of nucleic acid hybridization are disclosed by Sambrook et al. (supra).

In an alternative way of cloning the bovine adipocyte polypeptide gene of this invention, a library of expression vectors is prepared by cloning DNA or, more preferably, cDNA (from a cell capable of expressing the bovine adipocyte polypeptide) into an expression vector. The library is then screened for members capable of expressing a protein which binds to anti-bovine adipocyte polypeptide antibody, and which has a nucleotide sequence that is capable of encoding polypeptides that have the same amino acid sequence as the bovine adipocyte polypeptide of this invention, or fragments thereof. In this embodiment, DNA, or more preferably cDNA, is extracted and purified from a cell which is capable of expressing the bovine adipocyte polypeptide protein. The purified cDNA is fragmentized (by shearing, endonuclease digestion, etc.) to produce a pool of DNA or cDNA fragments. DNA or cDNA fragments from this pool are then cloned into an expression vector in order to produce a library of expression vectors whose members each contain a unique cloned DNA or cDNA fragment.

An "expression vector" is a vector which (due to the presence of appropriate transcriptional and/or translational control sequences) is capable of expressing a DNA (or cDNA) molecule which has been cloned into the vector and of thereby producing a polypeptide or protein. Expression vectors of the present invention may be either procaryotic or eukaryotic. Examples of suitable prokaryotic expression vectors include pASK75 (Biometra) or pET 21a–d (Novagen). Examples of suitable eukaryotic expression vectors include pcDNA3 or pRc/RSV (In Vitrogen, Inc.).

A DNA sequence encoding the bovine adipocyte polypeptide of the present invention, or its functional derivative, may be recombined with vector DNA in accordance with conventional techniques such as those disclosed by Sambrook, et al. (supra).

A nucleic acid molecule, such as DNA, is said to be "capable of expressing" a polypeptide if it contains nucleotide sequences which contain transcriptional and translational regulatory information and such sequences are "operably linked" to nucleotide sequences which encode the polypeptide. An operable linkage is a linkage in which the regulatory DNA sequences and the DNA sequence sought to be expressed are connected in such a way as to permit gene expression.

The precise nature of the regulatory regions needed for gene expression may vary from organism to organism, but shall in general include a promoter region which, in prokaryotes, contains both the promoter (which directs the initiation of RNA transcription) as well as the DNA sequences which, when transcribed into RNA, will signal the initiation of protein synthesis. A promoter is a double-stranded DNA or RNA molecule which is capable of binding RNA polymerase and promoting the transcription of the "operably linked" nucleic acid sequence. The promoter sequences of the present invention may be either prokaryotic, eukaryotic or viral. Strong promoters are, however, preferred. Suitable promoters are repressible, or more preferably, constitutive. Examples of suitable prokaryotic promoters include the tetracycline (Tet A) promoter for pASK75 and T7lac for pET21. Examples of suitable eukaryotic promoters include alpha actin or beta actin. Examples of suitable viral promoters include Rous sarcoma or cytomegala.

The present invention is also directed to an antibody specific for an epitope of the bovine adipocyte polypeptide of the present invention, and the use of such antibody to detect the presence of, or measure the quantity or concentration of the polypeptide, or a functional derivative thereof, in a cell, a cell or tissue extract, or a biological fluid. As used herein, the term "epitope" refers to that portion of any molecule capable of being bound by an antibody which can also be recognized by that antibody. Epitopes or "antigenic determinants" usually consist of chemically active surface groupings of molecules such as amino acids or sugar side chains and have specific three dimensional structural characteristics as well as specific charge characteristics. An antibody is said to be "capable of binding" a molecule if it is capable of specifically reacting with the molecule to thereby bind the molecule to the antibody.

The bovine adipocyte polypeptide of the present invention, or a functional derivative thereof, preferably having at least about 8 amino acids is used as an antigen for induction of a polyclonal antibody or monoclonal antibody (mAb). As used herein, an "antigen" is a molecule or a portion of a molecule capable of being bound by an antibody which is additionally capable of inducing an animal to produce antibody capable of binding to an epitope of that antigen. An antigen may have one, or more than one epitope. The specific reaction referred to above is meant to indicate that the antigen will react, in a highly selective manner, with its corresponding antibody and not with the multitude of other antibodies which may be evoked by other antigens.

The term "antibody" is meant to include polyclonal antibodies, monoclonal antibodies (mAbs), and chimeric antibodies. Polyclonal antibodies are heterogeneous populations of antibody molecules derived from the sera of animals immunized with an antigen. Monoclonal antibodies are a substantially homogeneous population of antibodies to specific antigenic epitopes. MAbs may be obtained by methods known to those skilled in the art. (See, for example Kohler and Milstein, Nature 256:495–497 (1975) and U.S. Pat. No. 4,376,110; de St. Groth, S. F. et al. J. Immunol. Methods, 35:1–21 (1980); and Hartlow, E. et al., Antibodies: A Laboratory Manual, Cold Spring Harbor Laboratory Press, Cold Spring Harbor, N.Y., 1988).

Chimeric antibodies are molecules different portions of which are derived from different animal species, such as those having a variable region derived from a bovine mAb and a murine immunoglobulin constant region. Chimeric antibodies and methods for their production are known in the art (Cabilly et al, Proc. Natl. Acad. Sci. USA 81:3273–3277 (1984); Morrison et al., Proc. Natl. Acad. Sci. USA 81:6851–6855 (1984); Boulianne et al., Nature 312:643–646 (1984); Neuberger et al., Nature 314:268–270 (1985); Liu et al., Proc. Natl. Acad. Sci. USA 84:3439–3443 (1987); Better et al., Science 240:1041–1043 (1988)). These references are hereby incorporated by reference.

The term "antibody" is also meant to include both intact molecules as well as fragments thereof, such as, for example, Fab and F(ab')$_2$, which are capable of binding antigen. Fab and F(ab')$_2$ fragments lack the Fc fragment of intact antibody, clear more rapidly from the circulation, and may have less non-specific tissue binding than an intact antibody (Wahl et al., J. Nucl. Med. 24:316–325 (1983)). Such fragments are typically produced by proteolytic cleavage, using enzymes such as papain (to produce Fab fragments) or pepsin (to produce F(ab')$_2$ fragments).

The reaction of the antibodies and the polypeptides of the present invention are detected by immunoassay methods well known in the art (See, for example, Hartlow et al. supra). The antibodies, or fragments of antibodies, useful in the present invention may be used to quantitatively or qualitatively detect the presence of cells which express the bovine adipocyte polypeptide protein. This can be accomplished by immunofluorescence techniques employing a fluorescently labeled antibody coupled with microscopy, flow cytometric, or fluorimetric detection.

The antibodies (or fragments thereof) useful in the present invention may be employed histologically, as in immunofluorescence or immunoelectron microscopy, for in situ detection of the bovine adipocyte polypeptide (i.e. leptin). In situ detection may be accomplished by removing a histological specimen from a subject, and providing a labeled antibody of the present invention to such a specimen. The antibody (or fragment) is preferably provided by applying or by overlaying the labeled antibody (or fragment) to a biological sample. Through the use of such a procedure, it is possible to determine not only the presence of the bovine adipocyte polypeptide of the present invention but also its distribution in the examined tissue. Using the present invention, those of ordinary skill will readily perceive that any of a wide variety of histological methods (such as staining procedures) can be modified in order to achieve such in situ detection.

Such assays for the bovine adipocyte polypeptide of the present invention typically comprise incubating a biological sample, such as a biological fluid, a tissue extract, freshly harvested or cultured cells containing adipogenic cells or adipocytes, in the presence of a detectably labeled antibody capable of identifying the bovine adipocyte polypeptide, and detecting the antibody by any of a number of techniques well-known in the art, such as enzyme immunoassays (EIA or ELISA) or radioimmunoassays (RIA).

The antibody molecules of the present invention may also be adapted for utilization in an immunometric assay, also known as a "two-site" or "sandwich" assay. In a typical immunometric assay, a quantity of unlabeled antibody (or fragment of antibody) is bound to a solid support (i.e., any support capable of binding antigen or antibodies) and a quantity of detectably labeled soluble antibody is added to permit detection and/or quantification of the ternary complex formed between solid-phase antibody, antigen, and labeled antibody.

The binding activity of a given lot of antibody to the bovine adipocyte polypeptide may be determined according to well known methods. Those skilled in the art will be able to determine operative and optimal assay conditions for each determination by employing routine experimentation.

Antibodies can be used in an immunoaffinity column to purify the binding adipocyte polypeptide of the invention by a one step procedure, using methods known in the art.

According to the present invention, cattle that are susceptible to fat deposition is treated with the bovine adipocyte polypeptide of the present invention to limit such fat deposition. This treatment may be performed in conjunction with other anti-adipogenic therapies. A typical regimen for treating cattle with a propensity for fat deposition comprises administration of an effective amount of the bovine adipocyte polypeptide administered over a period of time.

The bovine adipocyte polypeptide of the present invention may be administered by any means that achieves its intended purpose, preferably to alter feed intake or limit fat deposition in a subject. For example, administration may be by various parenteral routes including, but not limited to, subcutaneous, intravenous, intradermal, intramuscular, and intraperitoneal routes. Alternatively, or concurrently, administration may be by the oral route which may be accomplished by the use of genetically-altered feedstuffs, in which the bovine leptin gene has been inserted and expressed. Parenteral administration can be by bolus injection or by gradual perfusion over time such as by implant of osmotic delivery device. Preparations for parenteral administration include sterile aqueous or non-aqueous solutions, suspensions, and emulsions, which may contain auxiliary agents or excipients which are known in the art. Pharmaceutical compositions such as tablets and capsules can also be prepared according to routine methods.

It is understood that the dosage of bovine adipocyte polypeptide of the present invention administered may be dependent upon the age, sex, health, and weight of the recipient, kind of concurrent treatment, if any, frequency of treatment, and the nature of the effect desired. The most preferred dosage will be tailored to the individual subject, as is understood and determinable by one of skill in the art. The total dose required for each treatment may be administered by multiple doses or in a single dose. The bovine adipocyte polypeptide of the present invention may be administered alone or in conjunction with other therapeutics directed toward the regulation of feed intake and/or fat deposition.

In a preferred embodiment, the concentration of the bovine adipocyte polypeptide or mRNA of this invention is measured in a cell preparation, tissue extract or biological fluid of a subject as a means for determining the susceptibility or the propensity of the subject for fat deposition. The susceptibility of the subject to fat deposition is related to the level of the bovine adipocyte polypeptide, or its mRNA. Additionally, restriction fragment length polymorphisms in the bovine adipocyte gene will be used to predict fat deposition potential.

Another embodiment of the invention is evaluating the efficacy of a drug, or other agent, directed to the increase or decrease of feed intake by measuring the ability of the drug or agent to stimulate or suppress the production of the bovine adipocyte polypeptide or mRNA of this invention by a cell or cell line capable of producing such polypeptides or mRNAs. Preferred cells are cells of an adipogenic cell line. The antibodies, cDNA probe or riboprobe of the present invention are useful in the method for evaluating these drugs or other agents in that they can be employed to determine the amount of the bovine adipocyte polypeptide or mRNAs using one of the above-mentioned immunoassays.

An additional embodiment of the present invention is directed to assays for measuring the susceptibility of cattle to fat deposition based on measuring in a tissue or fluid from the subject the amount of the mRNA sequences present that encode the bovine adipocyte polypeptide, or a functional derivative thereof, preferably using an RNA or DNA hybridization assay. The susceptibility to fat deposition is related to the amount of such mRNA sequences present. For such assays, the source of the mRNA sequences is preferably the adipogenic cells of cattle. The preferred technique for measuring the amount of mRNA is a hybridization assay using RNA (e.g., ribonuclease protection assay) or DNA (e.g., Northern or slot blot assays) of complementary base sequence as probes.

Nucleic acid detection assays, especially hybridization assays, can be predicated on any characteristic of the nucleic acid molecule, such as its size, sequence, susceptibility to digestion by restriction endonucleases, etc. The sensitivity of such assays may be increased by altering the manner in which detection is reported or signaled to the observer. Thus, for example, assay sensitivity can be increased through the use of detectably labeled reagents. A wide variety of such labels have been used for this purpose. Kourilsky et al. (U.S. Pat. No. 4,581,333) describe the use of enzyme labels to increase sensitivity in a detection assay. Radioisotopic labels are disclosed by Falkow et al. (U.S. Pat. No. 4,358,535), and by Berninger (U.S. Pat. No. 4,446,237). Fluorescent labels (Albarella et al., EP 144914), chemical labels (Sheldon III et al., U.S. Pat. No. 4,582,789; Albarella et al., U.S. Pat. No. 4,563,417), modified bases (Miyoshi et al., EP 119448), etc. have also been used in an effort to improve the efficiency with which detection can be observed.

One method for overcoming the sensitivity limitation of nucleic acid concentration is to selectively amplify the nucleic acid whose detection is desired prior to performing the assay. Recombinant DNA methodologies capable of amplifying purified nucleic acid fragments have long been recognized. Typically, such methodologies involve the introduction of the nucleic acid fragment into a DNA or RNA vector, the clonal amplification of the vector, and the recovery of the amplified nucleic acid fragment. Examples of such methodologies are provided by Cohen et al. (U.S. Pat. No. 4,237,224), Maniatis, T., et al., etc.

Recently, an in vitro enzymatic method has been described which is capable of increasing the concentration of such desired nucleic acid molecules. This method has been referred to as the "polymerase chain reaction" or "PCR" (Mullis, K. et al., Cold Spring Harbor Symp. Quant. Biol. 51:263–273 (1986); Erlich H. et al., EP 50, 424; EP 84,796, EP 258,017, EP 237,362; Mullis, K., EP 201,184; Mullis K. et al., U.S. Pat. No. 4,683,202; Erlich, H., U.S. Pat. No. 4,582,788; and Saiki, R. et al., U.S. Pat. No. 4,683,194). The polymerase chain reaction provides a method for selectively increasing the concentration of a particular nucleic acid sequence even when that sequence has not been previously purified and is present only in a single copy in a particular sample. The method can be used to amplify either single- or double-stranded DNA. The essence of the method involves the use of two oligonucleotide probes to serve as primers for the template-dependent, polymerase mediated replication of a desired nucleic acid molecule.

Having now generally described the invention, the same will be more readily understood through reference to the following examples which are provided by way of illustration, and are not intended to be limiting of the present invention, unless specified.

EXAMPLE I

ISOLATION AND IDENTIFICATION OF BOVINE LEPTIN cDNA FROM ADIPOSE TISSUE

A. Isolation of Bovine Leptin cDNA

1. RNA Extraction

Total RNA was extracted from bovine adipose tissue, using a standard RNA extraction protocol: acidic guanidinium thiocyanate-phenol-chloroform extraction (Chomczynski and Sacchi, 1987, Analytic Biochemistry 162:156). Poly A$^+$ mRNA was then purified from total RNA by using a oligo(dT)-cellulose mini-column (Stratagene Cloning Systems, La Jolla, Calif.). In order to make a template for PCR amplification, poly A$^+$ mRNA was then reverse transcribed into single-stranded cDNA by using a reverse transcriptase (Gibco BRL, Gaithersburg, Md.).

2. PCR and Primer Information

The single-stranded bovine cDNA pool was used as a template to amplify bovine leptin cDNA in a PCR reaction with synthetic DNA primers based on the published mouse leptin cDNA sequence. Two pairs of oligonucleotide degenerate primers specific for the human and murine leptin gene were designed and synthesized (DNA International, Lake Oswego, Oreg.). The primers were designed to amplify the coding region of the bovine leptin gene, excluding the secretory signal at the 5'-terminal of the coding region). The forward primer has a sequence of 5'-GGA TCC GGT CTC AGG CCG TGC CYA TCC ARA AAG TCC-3' (contains a BsaI site), and the reverse primer has a sequence of 5'-GAA TTC AGC GCT GCA YYC AGG GCT RAS RTC-3' (contains a Eco47III site), where R=(A,G), S=(C,G), Y=(C, T). PCR was performed using the following conditions: 1×PCR buffer, 1.5 mM MgCl$_2$, 1 µM primers, 0.2 mM dNTPs and 5 units of Taq polymerase per 100-µl reaction. A total of 32 cycles were run with following cycling conditions: 94 C, 1 min; 55 C, 1.5 min; and 72C, 1.5 min. After running the PCR product on a 1% agarose gel, a band of 449 base pairs was obtained from the PCR-amplified bovine single-stranded cDNA as depicted in FIG. 6. Specifically, lane 1 of FIG. 6 contains the 449 base pair bovine leptin cDNA, lane 2 contains the pASK75 vector DNA, and lane 3 contains standard 100 base pair l adder . The size of the PCR product was consistent with the predicted size of the coding region of the bovine leptin gene. This PCR product was verified in a secondary PCR procedure.

B. Subcloning of the PCR Products into pASK75 Expression Vector

The bovine leptin cDNA obtained by the above procedures was cloned into specific restriction endonuclease cleavage sites (BsaI and Eco47III) of the pASK75 vector (Biometra Ltd., Tampa, Fla.). This vector, originally derived from pASK60, carries the promoter/operator region from the TetA resistance gene, and allows precise insertion of a gene and direct expression of a structural gene with the OmpA signal sequence and a Strep-tag polypeptide which is designed for affinity purification of the recombinant protein.

Briefly, the 449 bp PCR product was gel purified, and then partially cut by BsaI and Eco47III to facilitate in-frame expression of the inserted DNA. The vector pASK75 plasmid was cut with the same enzymes and then digested with bovine intestinal alkaline phosphatase (CIAP, Gibco BRL, ) to remove the 5'-phosphate group. This step prevents vector-vector ligations during the ligation reaction. After confirming by gel electrophoresis that the PCR product and vector were digested appropriately, the ligation was accomplished using T4 DNA ligase (Gibco BRL) with incubation at 14 C for 20 h. The recombinant bovine leptin DNA product was then transformed into an *E. coli* strain (XL-1 Blue, Stratagene Cloning Systems, La Jolla, Calif.) using the protocol recommended by the supplier. The *E. coli* were grown in culture, and the recombinant plasmid DNA induced to express the bovine leptin gene by adding anhydrotetracycline at a concentration below that required for antibiotic activity. The bovine leptin protein was then purified by either SDS-PAGE or Strep-Tag affinity chromatography. The recombinant plasmid DNA was also purified using a plasmid miniprep kit (Promega). The purified plasmid containing the bovine leptin insert was submitted to National Bioscience, Inc. for DNA sequencing to verify that the clone was the bovine leptin homologue and to establish homology with the human and murine leptin genes.

A clone obtained using the process described above, namely *E. coli* C1 was deposited with the American Type Culture Collection (ATCC), 12301 Parklawn Drive, Rockville, Md., 20852–1776, on Jun. 27, 1996, and have been designated ATCC No. 98087. This microorganism was deposited under the conditions of the Budapest Treaty on the International Recognition of Deposit of Microorganisms for the purpose of Patent Procedure. All restrictions on the availability to the public of the material so deposited will be irrevocably removed upon the granting of a patent. This deposit will be maintained for a time period of 30 years from the date of deposit or 5 years after the last request for the material, whichever is longer.

C. DNA and Protein Sequencing

Sequencing of the insert DNA (both sense and antisense strands) was performed by a commercial laboratory (National Bioscience, Inc.) using the standard Sanger's dideoxy-nucleotide method. Briefly, the PCR product containing the 449 bp band was separated on a 1% low-melting-agarose gel. The 449 bp band was cut from the gel, further purified using a Genecleaning kit (Bio101, Inc, Vista, Calif.), and submitted for sequencing. The sequences were then compared with the Genebank and other databses using the GCG software. The sequence data confirm that the 449 bp product from two independent clones shares approximately 87.6% homology with the human leptin cDNA (FIG. 2A) (SEQ ID NOS:3) and 84.9% with the mouse leptin cDNA (FIG. 2B ) (SEQ ID NO:3). The predicted amino acid sequence also shares approximately 87% homology with the human leptin protein (FIG. 3A) (SEQ ID NO:4) and approximately 86.3% homology with the murine leptin protein (FIG. 3B) (SEQ ID NO:4). Moreover, a portion of the predicted amino acid sequence was confirmed through amino terminal sequencing. Specifically, 30 amino acids comprising the N-terminal sequence have been obtained (FIG. 4) (SEQ ID NO:4). The actual amino acid sequence (i.e., the N-terminal sequence (FIG. 4)) (SEQ ID NO:4) shares approximately 100% homology with the human leptin protein (FIG. 5A) (SEQ ID NO:7), and approximately 100% homology with the murine leptin protein (FIG. 5B) (SEQ ID NO:8).

EXAMPLE II

ISOLATION OF mRNA CORRESPONDING TO BOVINE LEPTIN cDNA

Figure 7:
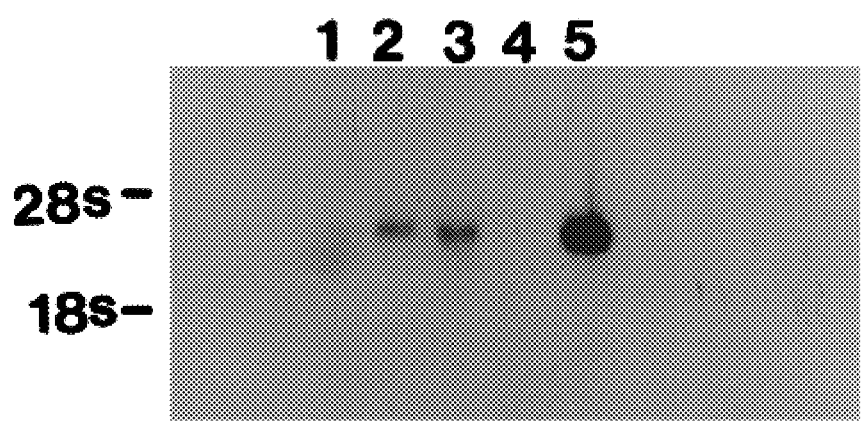
FIG. 7 depicts the Northern blot analysis of bovine leptin mRNA.

The bovine leptin cDNA was used as a probe for detection of the full length mRNA on a Northern blot containing bovine adipose tissue poly A+ mRNA and ob/ob mouse adipose total RNA (FIG. 7). The RNA samples were separated on a 1% formaldehyde agarose gel and then transferred to a nylon membrane (Zeta-probe, Biorad) by a capillary transfer method in 10×SSC (1.5M NaCl, 0.15 M Sodium Citrate, pH 7.0). The blot was hybridized with an alpha-[$^{32}$P] dCTP labeled bovine leptin cDNA in hybridization solution (Gibco BRL; 0.9 M NaCl, 0.09 M Sodium Citrate (pH 7.0), 0.01 M EDTA (pH 8.0), 5×Denhart's Solution (0.1% Ficoll, 0.1% polyvinylpyrolidone, 0.1% BSA), 0.5% SDS, 100 μg/ml sheared, denatured salmon sperm DNA) at 55C for 20 h. The blot was washed to a final stringency of 0.1×SSC (0.015M NaCl, 0.0015 M sodium citrate (pH 7), 0.1% SDS at 60 C and exposed to X-ray film. The bovine leptin mRNA (approximately 3,090 bp) was clearly evident in the bovine adipose tissue and an approximate 3,240 bp leptin mRNA was detected in the ob/ob mouse adipose tissue. As shown in FIG. 7, lanes 6–8 contain the ob/ob mouse adipose total RNA and lane 10 contains the bovine adipose poly A$^+$ mRNA.

Abundance of the bovine leptin mRNA was low; therefore, a more sensitive RNAse protection assay (RPA) was established to quantify bovine leptin mRNA in adipose tissue. Briefly, a T7 promoter DNA sequence was added to the antisense leptin ob primer via PCR with the sense primer as described in Example I. This modified antisense primer produced a 478 bp fragment containing the T7 promoter. A radiolabeled riboprobe was then generated by in vitro transcription with alpha-[$^{32}$P]-UTP and the 478 bp PCR fragment. The RPA was performed using a commercially available kit (RPA II, Ambion, Inc.). Hybridization was done with 50,000 cpm of the bovine leptin riboprobe and 10 μg of adipose total RNA for 20 h at 42–45 C. Single-stranded RNA was then digested by a 1:50 dilution of RNAse T1 for 30 min at 37C. After ethanol precipitation, the protected fragment was separated in a 5% polyacrylamide gel with 8M urea. The gel was then dried and exposed to X-ray film and a single 449 bp fragment was protected. Beta-actin was used as an internal control for standardization of the RPA results.

EXAMPLE III

ISOLATION OF GENOMIC DNA CLONE CORRESPONDING TO BOVINE LEPTIN

The bovine leptin cDNA was also used to screen a bovine genomic DNA library. Specifically, a bovine genomic library (Holstein dairy cow) was purchased from a commercial source (Stratagene, Inc.). The library, containing 2×10$^6$ plaque forming units (pfu) before amplification, was constructed in lambda FIX II vector with insert sizes of 9–23 kb. Procedures for genomic library screening were those recommended by the supplier. About 1.2×10$^6$ pfu were screened in the primary screening plates. Specifically, two sets of replica nylon filters were lifted from plates and prehybridized for 3 h at 40–42 C in 0.8 M NaCl, 0.02 M pipes (pH 6.5), 50% formamide, 0.5% SDS, and 100 μg/ml denatured, sonicated salmon sperm DNA. Filters were hybridized overnight with [alpha-$^{32}$P] dCTP labeled bovine leptin cDNA probe in hybridization buffer with the same composition as the prehybridization solution for 21 h. Filters were subsequently washed with a final stringency of 0.1× SSC, 0.1% SDS at 60 C for 30 min. After exposure to X-ray film, positive clones that showed signals on both replica filters were recovered from the agar plates, retitered and tested in secondary and tertiary screening using the same protocol. After three rounds of screening, four individual positive clones were identified for further use.

EXAMPLE IV

PURIFICATION OF THE BOVINE LEPTIN GENE PRODUCT

The polypeptide sequence encoded by the bovine leptin cDNA was purified by preparative SDS-polyacrylamide gel electrophoresis and then the recombinant protein band was electroeluted from the gel. The purified protein will be used for production of antibodies and development of ELISA and other assay methodologies.

EXAMPLE V

ANTIBODIES TO BOVINE LEPTIN AND THEIR USE TO DETECT BOVINE LEPTIN IN ADIPOGENIC CELLS

Polyclonal and/or monoclonal antibodies are produced with the recombinant bovine leptin protein. The techniques used for producing, screening, detecting, and/or quantifying antibodies or leptin are discussed extensively in "Antibodies: a laboratory manual" (Harlow et al., 1988, Cold Spring Harbor laboratory). All media or medium components, mouse or cell strains (e.g. BALB/C mouse, sp2/0 myeloma cells, JA744A. 1 macrophages etc.) are commercially available.

A. Immunization of Animals

1. Rabbits

Purified bovine leptin protein is injected into rabbits for production of polyclonal antibodies. Specifically, each rabbit receives repeated subcutaneous injections with antigen in Freund's complete adjuvant followed by at least 1 booster injection of about 200 μg to 1 mg. When the serum titer of the immunized rabbits is sufficiently high when tested using the bovine leptin as antigen, rabbit serum is harvested as the polyclonal antiserum for bovine leptin.

2. BALB/C mice (4-week old)

Purified bovine leptin protein is injected into BALB/C mice for production of monoclonal antibodies. Specifically, each mouse is injected with about 50 μg bovine leptin protein with Ribi's S-TDCM adjuvants (RIBI ImmunoChem Research, Inc., Hamilton, Mont.). The number of injections depends on the titer of the antibody in the serum of immunized mice as determined by ELISA using bovine leptin as the antigen. In the course of producing monoclonal antibodies against bovine leptin protein, the spleens of immunized mice are used to prepare spleenocytes. Hybridoma cells will be made by fusing the spleenocytes with sp2/0 myeloma cells (treated with 8-Azaguanine containing medium) in the presence of 50% PEG-1500. Hybridoma cells are incubated in selection HAT (hypoxanthine, aminopterin, and thymidine) medium. Subsequent screening for positive clones uses the recombinant bovine leptin as antigen in ELISA or Western blot methodology. Positive clones that produce strong anti-bovine-leptin antibody is characterized for specificity, subtype, affinity, binding sites, etc.

When large quantities of purified antibody are needed, the positive clones are cultured in large scale and antibody purified from the culture supernatant, or injected into the intraperitoneal cavity of BALB/C mice for production of ascites. The latter procedure requires about $1-2\times10^6$ hybridoma cells per mouse, and usually takes about 7–14 days. Large quantities of antibody is purified from ascites by techniques such as ammonium sulphate precipitation and ion exchange chromatography (e.g. DEAE-Trisacryl M).

Having now fully described this invention, it will be appreciated by those skilled in the art that the same can be performed within a wide range of equivalent parameters, concentrations, and conditions without departing from the spirit and scope of the invention and without undue experimentation. While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

What is claimed is:

1. An isolated single or double-stranded DNA molecule consisting of a nucleotide sequence which encodes a bovine adipocyte polypeptide leptin having the amino acid sequence of SEQ ID NO:4, or the complement to said DNA molecule.

2. The DNA molecule of claim 1 consisting of the nucleotide sequence of SEQ ID NO:3.

3. An expression vector comprising the DNA molecule of claim 1.

4. The vector according to claim 3 wherein said vector is a plasmid.

5. An expression vector comprising the DNA molecule of claim 2.

6. The vector according to claim 5 wherein said vector is a plasmid.

7. A host cell transformed or transfected with the vector according to claim 3.

8. A host cell transformed or transfected with the plasmid according to claim 4.

9. A host cell transformed or transfected with the vector according to claim 5.

10. A host cell transformed or transfected with the plasmid according to claim 6.

11. An isolated mRNA molecule consisting of a nucleotide sequence that encodes a bovine adipocyte polypeptide leptin having the amino acid sequence of SEQ ID NO:4.

12. An isolated mRNA molecule encoding a bovine adipocyte polypeptide leptin, the mRNA sequence encoded by the nucleotide sequence of SEQ ID NO:3.

13. A bovine adipocyte polypeptide leptin encoded by a nucleic acid molecule consisting of the nucleotide sequence of SEQ ID NO:3.

14. The bovine adipocyte polypeptide leptin of claim 13 in which the polypeptide has the amino acid sequence of SEQ ID NO:4.

* * * * *

SEQUENCE LISTING

```
(1) GENERAL INFORMATION:

(iii) NUMBER OF SEQUENCES: 8

(2) INFORMATION FOR SEQ ID NO:1:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO:1:

GGATCCGGTC TCAGGCCGTG CCYATCCARA AAGTCC                                    36

(2) INFORMATION FOR SEQ ID NO:2:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO:2:

GAATTCAGCG CTGCAYYCAG GGCTRASRTC                                           30

(2) INFORMATION FOR SEQ ID NO:3:

(i) SEQUENCE CHARACTERISTICS:
        (A) LENGTH: 449 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 6..443
```

(xi) SEQUENCE DESCRIPTION: SEQ ID NO:3:

```
AGGCC GTG CCT ATC CAG AAA GTC CAG GAT GAC ACC AAA ACC CTC ATC        47
      Val Pro Ile Gln Lys Val Gln Asp Asp Thr Lys Thr Leu Ile
        1               5                  10

AAG ACA ATT GTC ACC AGG ATC AAT GAC ATC TCA CAC ACG CAG TCC GTC      95
Lys Thr Ile Val Thr Arg Ile Asn Asp Ile Ser His Thr Gln Ser Val
 15              20                  25                  30

TCC TCC AAA CAG AGG GTC ACT GGT TTG GAC TTC ATC CCT GGG CTC CAC     143
Ser Ser Lys Gln Arg Val Thr Gly Leu Asp Phe Ile Pro Gly Leu His
             35                  40                  45

CCT CTC CTG AGT TTG TCC AAG ATG GAC CAG ACA TTG GCG ATC TAC CAA     191
Pro Leu Leu Ser Leu Ser Lys Met Asp Gln Thr Leu Ala Ile Tyr Gln
             50                  55                  60

CAG ATC CTC ACC AGT CTG CCT TCC AGA AAT GTG GTC CAA ATA TCC AAT     239
Gln Ile Leu Thr Ser Leu Pro Ser Arg Asn Val Val Gln Ile Ser Asn
             65                  70                  75

GAC CTG GAG AAC CTC CGG GAC CTT CTC CAC CTG CTG GCC GCC TCC AAG     287
Asp Leu Glu Asn Leu Arg Asp Leu Leu His Leu Leu Ala Ala Ser Lys
 80                  85                  90

AGC TGC CCC TTG CCG CAG GTC AGG GCC CTG GAG AGC TTG GAG AGC TTG     335
Ser Cys Pro Leu Pro Gln Val Arg Ala Leu Glu Ser Leu Glu Ser Leu
 95              100                 105                 110

GGT GTC GTC CTG GAA GCC TCC CTC TAC TCC ACC GAG GTG GTG GCC CTG     383
Gly Val Val Leu Glu Ala Ser Leu Tyr Ser Thr Glu Val Val Ala Leu
                 115                 120                 125

AGC CGG CTG CAG GGG TCA CTA CAG GAC ATG TTG CGG CAG CTG GAC CTC     431
Ser Arg Leu Gln Gly Ser Leu Gln Asp Met Leu Arg Gln Leu Asp Leu
             130                 135                 140

AGC CCT GAA TGC AGCGCT                                               449
Ser Pro Glu Cys
        145
```

(2) INFORMATION FOR SEQ ID NO:4:

(i) SEQUENCE CHARACTERISTICS:
        (A) LENGTH: 146 amino acids
        (B) TYPE: amino acid
        (D) TOPOLOGY: linear (ii) MOLECULE TYPE: protein (xi) SEQUENCE DESCRIPTION: SEQ ID NO:4:

```
Val Pro Ile Gln Lys Val Gln Asp Asp Thr Lys Thr Leu Ile Lys Thr
 1               5                  10                  15

Ile Val Thr Arg Ile Asn Asp Ile Ser His Thr Gln Ser Val Ser Ser
             20                  25                  30

Lys Gln Arg Val Thr Gly Leu Asp Phe Ile Pro Gly Leu His Pro Leu
         35                  40                  45

Leu Ser Leu Ser Lys Met Asp Gln Thr Leu Ala Ile Tyr Gln Gln Ile
 50                  55                  60

Leu Thr Ser Leu Pro Ser Arg Asn Val Val Gln Ile Ser Asn Asp Leu
 65                  70                  75                  80

Glu Asn Leu Arg Asp Leu Leu His Leu Leu Ala Ala Ser Lys Ser Cys
                 85                  90                  95

Pro Leu Pro Gln Val Arg Ala Leu Glu Ser Leu Glu Ser Leu Gly Val
             100                 105                 110

Val Leu Glu Ala Ser Leu Tyr Ser Thr Glu Val Val Ala Leu Ser Arg
         115                 120                 125
```

Leu Gln Gly Ser Leu Gln Asp Met Leu Arg Gln Leu Asp Leu Ser Pro
    130                 135                 140

Glu Cys
145

(2) INFORMATION FOR SEQ ID NO:5:

(i) SEQUENCE CHARACTERISTICS:
        (A) LENGTH: 445 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

```
AAGCTGTGCC CATCCAAAAA GTCCAAGATG ACACCAAAAC CCTCATCAAG ACAATTGTCA    60

CCAGGATCAA TGACATTTCA CACACGCAGT CAGTCTCCTC CAAACAGAAA GTCACCGGTT   120

TGGACTTCAT TCCTGGGCTC CACCCCATCC TGACCTTATC CAAGATGGAC CAGACACTGG   180

CAGTCTACCA ACAGATCCTC ACCAGTATGC CTTCCAGAAA CGTGATCCAA ATATCCAACG   240

ACCTGGAGAA CCTCCGGGAT CTTCTTCACG TGCTGGCCTT CTCTAAGAGC TGCCACTTGC   300

CCTGGGCCAG TGGCCTGGAG ACCTTGGACA GCCTGGGGGG TGTCCTGGAA GCTTCAGGCT   360

ACTCCACAGA GGTGGTGGCC CTGAGCAGGC TGCAGGGGTC TCTGCAGGAC ATGCTGTGGC   420

AGCTGGACCT CAGCCCTGGG TGCTG                                        445
```

(2) INFORMATION FOR SEQ ID NO:6:

(i) SEQUENCE CHARACTERISTICS:
        (A) LENGTH: 445 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:6:

```
AAGCAGTGCC TATCCAGAAA GTCCAGGATG ACACCAAAAC CCTCATCAAG ACCATTGTCA    60

CCAGGATCAA TGACATTTCA CACACGCAGT CGGTATCCGC CAAGCAGAGG GTCACTGGCT   120

TGGACTTCAT TCCTGGGCTT CACCCCATTC TGAGTTTGTC CAAGATGGAC CAGACTCTGG   180

CAGTCTATCA ACAGGTCCTC ACCAGCCTGC CTTCCCAAAA TGTGCTGCAG ATAGCCAATG   240

ACCTGGAGAA TCTCCGAGAC CTCCTCCATC TGCTGGCCTT CTCCAAGAGC TGCTCCCTGC   300

CTCAGACCAG TGGCCTGCAG AAGCCAGAGA GCCTGGATGG CGTCCTGGAA GCCTCACTCT   360

ACTCCACAGA GGTGGTGGCT TTGAGCAGGC TGCAGGGCTC TCTGCAGGAC ATTCTTCAAC   420

AGTTGGATGT TAGCCCTGAA TGCTG                                        445
```

(2) INFORMATION FOR SEQ ID NO:7:

(i) SEQUENCE CHARACTERISTICS:
        (A) LENGTH: 167 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:7:

Met His Trp Gly Thr Leu Cys Gly Phe Leu Trp Leu Trp Pro Tyr Leu
1               5                   10                  15

```
Phe Tyr Val Gln Ala Val Pro Ile Gln Lys Val Gln Asp Asp Thr Lys
                20                  25                  30

Thr Leu Ile Lys Thr Ile Val Thr Arg Ile Asn Asp Ile Ser His Thr
            35                  40                  45

Gln Ser Val Ser Ser Lys Gln Lys Val Thr Gly Leu Asp Phe Ile Pro
 50                  55                  60

Gly Leu His Pro Ile Leu Thr Leu Ser Lys Met Asp Gln Thr Leu Ala
 65                  70                  75                   80

Val Tyr Gln Gln Ile Leu Thr Ser Met Pro Ser Arg Asn Val Ile Gln
                85                  90                  95

Ile Ser Asn Asp Leu Glu Asn Leu Arg Asp Leu Leu His Val Leu Ala
            100                 105                 110

Phe Ser Lys Ser Cys His Leu Pro Trp Ala Ser Gly Leu Glu Thr Leu
            115                 120                 125

Asp Ser Leu Gly Gly Val Leu Glu Ala Ser Gly Tyr Ser Thr Glu Val
            130                 135                 140

Val Ala Leu Ser Arg Leu Gln Gly Ser Leu Gln Asp Met Leu Trp Gln
145                 150                 155                 160

Leu Asp Leu Ser Pro Gly Cys
                165

(2) INFORMATION FOR SEQ ID NO:8:

(i) SEQUENCE CHARACTERISTICS:
         (A) LENGTH: 167 amino acids
         (B) TYPE: amino acid
         (C) STRANDEDNESS:
         (D) TOPOLOGY: linear (ii) MOLECULE TYPE: protein (xi) SEQUENCE DESCRIPTION: SEQ ID NO:8:

Met Cys Trp Arg Pro Leu Cys Arg Phe Leu Trp Leu Trp Ser Tyr Leu
 1               5                  10                  15

Ser Tyr Val Gln Ala Val Pro Ile Gln Lys Val Gln Asp Asp Thr Lys
                20                  25                  30

Thr Leu Ile Lys Thr Ile Val Thr Arg Ile Asn Asp Ile Ser His Thr
            35                  40                  45

Gln Ser Val Ser Ala Lys Gln Arg Val Thr Gly Leu Asp Phe Ile Pro
 50                  55                  60

Gly Leu His Pro Ile Leu Ser Leu Ser Lys Met Asp Gln Thr Leu Ala
 65                  70                  75                   80

Val Tyr Gln Gln Val Leu Thr Ser Leu Pro Ser Gln Asn Val Leu Gln
                85                  90                  95

Ile Ala Asn Asp Leu Glu Asn Leu Arg Asp Leu Leu His Leu Leu Ala
            100                 105                 110

Phe Ser Lys Ser Cys Ser Leu Pro Gln Thr Ser Gly Leu Gln Lys Pro
            115                 120                 125

Glu Ser Leu Asp Gly Val Leu Glu Ala Ser Leu Tyr Ser Thr Glu Val
            130                 135                 140

Val Ala Leu Ser Arg Leu Gln Gly Ser Leu Gln Asp Ile Leu Gln Gln
145                 150                 155                 160

Leu Asp Val Ser Pro Glu Cys
                165
```